US012779002B1

(12) United States Patent
Zaitone et al.

(10) Patent No.: US 12,779,002 B1
(45) Date of Patent: Nov. 3, 2026

(54) PREPARATION OF MACADAMIA OIL/WATER NANOEMULSION FOR USE IN A PALATABLE FORMULA FOR TREATING INFLAMMATORY DISEASES

(71) Applicant: University of Tabuk, Tabuk (SA)

(72) Inventors: Sawsan Abobakr Abohashem Zaitone, Tabuk (SA); Abdullah Odah Faraj Alatawi, Tabuk (SA); Mona Kamel Eed Qushawy, Tabuk (SA); Reem Shelweeh Homoud Alshaman, Tabuk (SA)

(73) Assignee: University of Tabuk, Tabuk (SA)

( * ) Notice: Subject to any disclaimer, the term of this patent is extended or adjusted under 35 U.S.C. 154(b) by 0 days.

(21) Appl. No.: 19/251,967

(22) Filed: Jun. 27, 2025

(51) Int. Cl.

| | |
|---|---|
| ***A61K 36/18*** | (2006.01) |
| ***A61K 9/107*** | (2006.01) |
| ***A61K 47/10*** | (2017.01) |
| ***A61K 47/26*** | (2006.01) |

(52) U.S. Cl.
CPC ............ *A61K 36/18* (2013.01); *A61K 9/1075* (2013.01); *A61K 47/10* (2013.01); *A61K 47/26* (2013.01)

(58) Field of Classification Search
CPC ......... A61P 1/16; A61K 36/18; A61K 9/1075; A61K 47/10; A61K 47/26
See application file for complete search history.

(56) References Cited

U.S. PATENT DOCUMENTS 11,254,773 B2 2/2022 Helgeson et al.

FOREIGN PATENT DOCUMENTS

EP 3 995 133 A1 5/2022
IN 477325 12/2023

OTHER PUBLICATIONS

Somwongin S, Chaiyana W. Clinical Efficacy in Skin Hydration and Reducing Wrinkles of Nanoemulsions Containing Macadamia integrifolia Seed Oil. Nanomaterials (Basel). Apr. 20, 2024;14(8):724, 16 pages. doi: 10.3390/nano14080724. PMID: 38668218; PMCID: PMC11054140. (Year: 2024).*

Shuai X, et al. Hypolipidemic effects of macadamia oil are related to AMPK activation and oxidative stress relief: In vitro and in vivo studies. Food Res Int. Jun. 2023; 168: 112772, 12 pages. doi: 10.1016/j.foodres.2023.112772. Epub Mar. 25, 2023. PMID: 37120222. (Year: 2023).*

Szumała P, et al. Microemulsion Delivery Systems with Low Surfactant Concentrations: Optimization of Structure and Properties by Glycol Cosurfactants. Mol Pharm. Jan. 2, 2023;20(1): 232-240, 9 pages. doi: 10.1021/acs.molpharmaceut.2c00599. Epub Nov. 10, 2022. PMID: 36354760; PMCID: PMC9811459. (Year: 2023).*

Jaiswal M, et al. Nanoemulsion: an advanced mode of drug delivery system. 3 Biotech. Apr. 2015;5(2):123-127. doi: 10.1007/s13205-014-0214-0. Epub Apr. 8, 2014. PMID: 28324579; PMCID: PMC4362737. (Year: 2015).*

Asmawati, et al., "Characteristics of Cinnamaldehyde Nanoemulsion Prepared using APV-High Pressure Homogenizer and Ultra Turrax", AIP Conference Proceedings, 1614, Sep. 3, 2014, pp. 244-250.

Suvimol Somwongin, et al., "Clinical Efficacy in Skin Hydration and Reducing Wrinkles of Nanoemulsions Containing. *Macadmia integrifolia* Seed Oil", Nanomaterials 2024, vol. 14, 724, Apr. 20, 2024, 16 pages.

* cited by examiner

*Primary Examiner* — Aaron J Kosar
*Assistant Examiner* — Jennifer Lynn Cain
(74) *Attorney, Agent, or Firm* — Oblon, McClelland, Maier & Neustadt, L.L.P.

(57) ABSTRACT

A method of treating a non-alcoholic fatty liver disease including administering a macadamia oil nanoemulsion to a subject in need of treatment for the non-alcoholic fatty liver disease. The macadamia oil nanoemulsion includes 25 v/v % of a macadamia oil, and a surfactant mixture, a hydrophilic emulsifier and a cosurfactant in a volume ratio of 1:3 to 3:1. The macadamia oil nanoemulsion has an average droplet size of 200 nm or less, a polydispersity index of less than 0.50, and an absolute zeta potential of more than 22 mV.

4 Claims, 7 Drawing Sheets

PREPARATION OF MACADAMIA OIL/WATER NANOEMULSION FOR USE IN A PALATABLE FORMULA FOR TREATING INFLAMMATORY DISEASES

BACKGROUND

Technical Field

The present disclosure is directed towards fatty liver disease management, and more particularly, towards a method of treating non-alcoholic fatty liver disease using macadamia oil nanoemulsion.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present disclosure.

Non-alcoholic fatty liver disease (NAFLD) is a condition where fat builds up in the liver without excessive alcohol consumption. NAFLD progresses through a series of stages, involving multiple pathways and molecular mechanisms. The initial stage of NAFLD is caused by insulin resistance, which leads to excess free fatty acids (FFAs) being stored as triglycerides. As NAFLD progresses, oxidative stress and endoplasmic reticulum (ER) stress lead to lipid peroxidation. This process produces cytokines that promote inflammation, fibrosis, and cell death. Inflammation and fibrosis progress from periportal to bridging fibrosis, and eventually to excessive scarring of the liver, known as cirrhosis. NAFLD may also progress to hepatocellular carcinoma (HCC).

Strategies for slowing the progression of NAFLD are aiming at decreasing liver fat and inflammation. While there is no standard line of treatment for NAFLD, most recognize lifestyle changes, such as weight loss, healthy diet, and exercise, to be the primary line of treatment for NAFLD patients. Currently, there are no specific medications approved to treat NAFLD, therefore, there exists a need to develop safe, effective, and inexpensive therapies for treating NAFLD.

Accordingly, it is one object of the present disclosure to provide a method for treating NAFLD that may circumvent the drawbacks and limitations, such as high cost, low safety, and poor therapeutic efficiency, of methods and materials known in the art.

SUMMARY

In an exemplary embodiment, a method of treating non-alcoholic fatty liver disease is described. The method comprises administering a macadamia oil nanoemulsion to a subject in need thereof. The macadamia oil nanoemulsion comprises 25 percent by volume (v/v %) of a macadamia oil based on a total volume of the macadamia oil nanoemulsion, and a surfactant mixture, further comprising a hydrophilic emulsifier and a cosurfactant in a volume ratio of 1:3 to 3:1. The macadamia oil nanoemulsion has a preferable average droplet size of less than 200 nanometers (nm), a preferable polydispersity index (PDI) of less than 0.50, and a preferable absolute zeta potential in the range of −22.31±1.40 to −33.71±1.80. The hydrophilic emulsifier is a polysorbate and the cosurfactant is at least one selected from the group consisting of an ethylene glycol, a propylene glycol, a triethylene glycol, and a diethylene glycol. In the subject with hepatic injury, administration of the macadamia oil nanoemulsion results in a decreased expression of α-SMA protein in comparison to a control group In some embodiments, the hydrophilic emulsifier is present in the surfactant mixture in an amount of 5 to 15 v/v % based on a total volume of the macadamia oil nanoemulsion.

In some embodiments, the cosurfactant is present in the surfactant mixture in an amount of 10 to 30 v/v % based on a total volume of the macadamia oil nanoemulsion.

In some embodiments, the nanoemulsion comprises 25 v/v % of the macadamia oil based on a total volume of the macadamia oil nanoemulsion.

In some embodiments, the hydrophilic emulsifier is at least one selected from the group consisting of polysorbate 20, polysorbate 40, and polysorbate 80.

In some embodiments, the macadamia oil nanoemulsion further comprises 45 to 65 v/v % of water based on a total volume of the macadamia oil nanoemulsion.

In some embodiments, the macadamia oil nanoemulsion has a hydrophilic to lipophilic balance (HLB) of 10 to 20.

In some embodiments, the macadamia oil nanoemulsion has a preferable viscosity of 2.57±0.61 to 8.67±0.45 cP.

In some embodiments, the macadamia oil nanoemulsion has a creaming index of 0.50% to 2.75%.

In some embodiments, the macadamia oil nanoemulsion comprises spherical droplets.

In some embodiments, the macadamia oil nanoemulsion has a preferable PDI of 0.342±0.02 to 0.475±0.01.

In some embodiments, the macadamia oil nanoemulsion has a preferable viscosity of 2.57±0.61 to 8.67±0.45 cP.

In some embodiments, the method of administering the macadamia oil nanoemulsion comprises administering 0.8 mL/kg or less at least one to four times per week to a subject in need thereof.

In some embodiments, the macadamia oil nanoemulsion has a preferable absolute zeta potential of −22.31±1.40 to −33.71±1.80.

In some embodiments, the macadamia oil nanoemulsion has a preferable creaming index of 0.52±0.03 to 3.16±0.98%

In some embodiments, the macadamia oil nanoemulsion has a preferable average droplet size of 132.25±1.52 to 195.46±4.89 nm.

In some embodiments, the macadamia oil nanoemulsion inhibits a formation of karyorrhectic and/or karyolitic nuclei in liver cells of the subject compared to a macadamia oil.

In some embodiments, the macadamia oil nanoemulsion reduces congestion and/or dilation in liver central veins and portal tracts of the subject compared to a macadamia oil.

In some embodiments, the macadamia oil nanoemulsion decreases an amount of collagen fibers around liver central veins and blood sinusoids of the subject compared to a macadamia oil.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
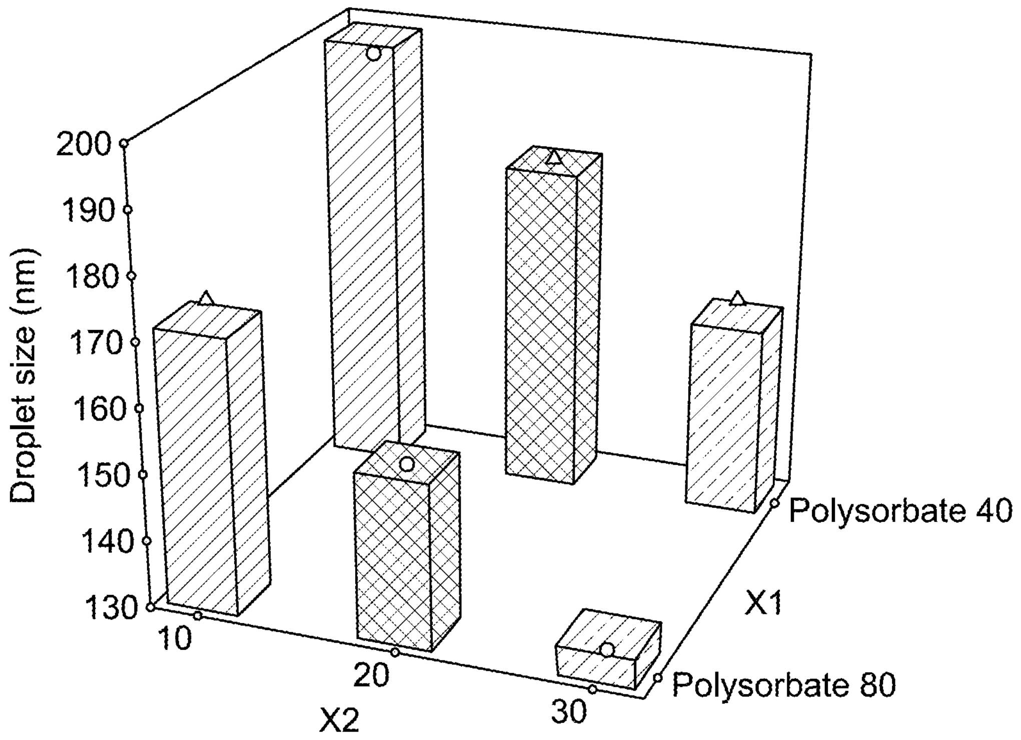
FIG. 1A is a graph depicting the effect of the concentration of the surfactant mixture and surfactant type on droplet size, according to some embodiments.

In the following description, it is understood that other embodiments may be utilized, and structural and operational changes may be made without departure from the scope of the present embodiments disclosed herein.

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

Furthermore, the terms "approximately," "approximate," "about," and similar terms generally refer to ranges that include the identified value within a margin of 20%, 10%, or preferably 5%, and any values therebetween.

As used herein, the term "disease" refers to the specific, measurable, and often pathological disturbance in the normal structure or function of an organism, particularly within its cells, tissues, or organs, which leads to a deviation from a state of health. This condition is often characterized by a set of signs, symptoms, or measurable abnormalities that can be identified through clinical assessment, laboratory tests, or imaging techniques. A disease occurs when an organism's physiological processes or cellular functions are disrupted due to factors like infections, genetic mutations, environmental influences, or other underlying causes, leading to a pathological state.

As used herein, the term "treating" refers to the application of medical or therapeutic interventions aimed at alleviating, curing, managing, or preventing a disease, condition, or injury. Treatment involves the use of various methods, such as pharmaceuticals, surgical procedures, physical therapies, lifestyle modifications, or other medical practices, based on the underlying cause and nature of the condition. Treating is the process of actively intervening to restore health or improve the functioning of the body by addressing the disease's symptoms, underlying mechanisms, or both. Treatment can be curative, aimed at eliminating the disease entirely; palliative, aimed at alleviating symptoms without curing the disease; or preventive, aimed at preventing the onset of a disease or condition.

As used herein, the term "patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a subject is human.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device (e.g., a mini-osmotic pump) to a subject. Administration is by any route, including parenteral and transmucosal (e.g., buccal, sublingual, palatal, gingival, nasal, vaginal, rectal, or transdermal). Parenteral administration includes, but is not limited to, intravenous, intramuscular, intra-arteriole, intradermal, subcutaneous, intraperitoneal, intraventricular, and intracranial administration. Other modes of delivery include, but are not limited to, the use of liposomal formulations, intravenous infusion, transdermal patches, etc.

As used herein, the term "absolute zeta potential" refers to the magnitude of the electrostatic potential difference at the slipping plane of a particle in a colloidal system. It measures the strength of electrostatic repulsion or attraction between particles, influencing the stability of suspensions. A higher absolute zeta potential typically indicates greater stability, as it prevents particle aggregation. It is expressed in millivolts (mV).

As used herein, the term "surfactant" refers to a compound that lowers the surface tension (or interfacial tension) between two liquids, between a liquid and a gas, or between a liquid and a solid. A surfactant molecule comprises one or more hydrophilic head units attached to one or more hydrophobic tails.

As used herein, the term "hydrophilic emulsifier" refers to the type of surfactant that has an affinity for water and helps to stabilize an emulsion by reducing the surface tension between two immiscible liquids, such as oil and water. The hydrophilic part of the emulsifier interacts with the water phase, while the hydrophobic part interacts with the oil phase. This dual affinity allows the emulsifier to form a stable mixture of oil and water, preventing the phases from separating.

As used herein, the term "cosurfactant" refers to the additional surfactant used alongside a primary surfactant to improve the stability and performance of emulsions, micelles, or other surfactant-based formulations. While the primary surfactant may be responsible for reducing surface tension, the cosurfactant aids in enhancing the overall efficiency, stability, and spreading properties of the formulation. Cosurfactants are often used to modify the properties of the system, such as increasing the solubility of hydrophobic substances, improving the consistency of emulsions, or lowering the critical micelle concentration (CMC) in the formulation. They can be hydrophobic or hydrophilic depending on the specific requirements of the product.

As used herein, the term "critical micelle concentration (CMC)" refers to the surfactant concentration at which micelle formation is first seen in the solution. The CMC is used to determine the minimum amount of surfactant needed to reduce the maximum surface tension of a substance. Before reaching the CMC, the surface tension changes strongly with the concentration of the surfactant. After reaching the CMC, the surface tension remains relatively constant or changes with a lower slope.

As used herein, the term "creaming index" refers to the measure of the stability of an emulsion, particularly in relation to the separation of its components, such as the dispersion of oil and water phases. It quantifies the degree of creaming or separation that occurs when the emulsion is allowed to stand, typically under gravitational forces. The creaming index is expressed as a percentage and is calculated by comparing the height of the cream layer to the total height of the emulsion after a certain period. A higher creaming index indicates greater separation, while a lower value indicates a more stable emulsion.

As used herein, the term "viscosity" refers to the measure of a fluid's resistance to flow or deformation. It quantifies the internal friction between molecules in the fluid, which affects how easily it flows under an applied force. Higher viscosity indicates thicker or more resistant fluids, while lower viscosity indicates thinner or more fluid-like substances. In pharmaceutical applications, the viscosity of a nanoemulsion can influence its skin penetration and absorption characteristics.

As used herein, the term "polydispersity index" or "PDI" refers to the measure of the distribution of the particle sizes within a given sample. The numerical value of PDI ranges from 0.0 (for a perfectly uniform sample with respect to the particle size) to 1.0 (for a highly polydisperse sample with multiple particle size populations). PDI values may vary due to the particle size distribution of a sample or the presence of agglomerates or aggregates in the sample. PDI is measured using dynamic light scattering (DLS). Successful formulation of safe, stable, and efficient nanoemulsion require the nanoemulsion to have a substantially monodisperse population of microparticles having a certain droplet size. The particle size distribution may be controlled by the selection of the surfactants and co-surfactants utilized during preparation of the nanoemulsion. PDI may be measured according to International Standards Organization (ISO) 22,412:2017. The ISO has established that PDI values $<0.05$ are more common to monodisperse samples, while PDI values $>0.7$ more common to broad size (i.e., polydisperse) distribution of particles.

As used herein, the term "hydrophilic-lipophilic balance (HLB)" refers to the numerical scale that measures the relative balance between the hydrophilic (water-attracting) and lipophilic (oil-attracting) regions of a surfactant. It indicates the surfactant's ability to emulsify oil in water or water in oil. HLB values range from 0 to 20. An HLB of 0 to 10 is more lipophilic (oil-soluble) and suitable for water-in-oil emulsions, while an HLB of 10 to 20 is more hydrophilic (water-soluble) and suitable for oil-in-water emulsions.

A method of treating a non-alcoholic fatty liver disease (NAFLD) is described. Non-alcoholic fatty liver disease is a condition characterized by the accumulation of excess fat, not caused by excessive alcohol consumption, in the liver cells of individuals. This fat buildup can lead to inflammation and damage to liver tissue over time. NAFLD is often associated with metabolic conditions such as obesity, type 2 diabetes (diabetes mellitus), high cholesterol, and high blood pressure. NAFLD can range from steatosis (fatty liver), which typically has no symptoms and is considered a benign condition, to non-alcoholic steatohepatitis (NASH), which involves inflammation and liver cell damage. When fat builds up in the liver, it triggers an inflammatory response causing the immune cells to release chemicals (e.g., cytokines) that damage liver cells and promote further inflammation. If the inflammation persists, it progresses from NAFLD to NASH, which is characterized by both fat accumulation and significant liver cell damage with inflammatory cell infiltration. Chronic inflammation in NASH can lead to fibrosis, where the liver attempts to repair itself by forming scar tissue. If this process continues, it can result in cirrhosis, a severe stage of liver scarring that significantly impairs liver function.

In one embodiment, the method comprises administering a macadamia oil nanoemulsion for NAFLD to a subject in need thereof. In another embodiment, the method comprises administering 0.8 mL/kg or less at least one to four times per week to a subject in need thereof. In some embodiments, the method comprises administering. In a preferred embodiment, the method comprises administering 2 mL/rat three times per week to a subject in need thereof.

In one embodiment, the macadamia oil nanoemulsion comprises macadamia oil. Macadamia oil, also known as macadamia nut oil, is a non-volatile oil extracted from the nuts of the macadamia tree (*Macadamia integrifolia*), indigenous to Australia. Macadamia oil can be extracted from macadamia nuts using a variety of methods including, but not limited to, cold pressing, solvent extraction, and supercritical $CO_2$ extraction. During cold pressing, a hydraulic press or screw press is utilized to extract oil from the nut at a temperature below 30° C. This method produces extra virgin macadamia oil and partially defatted meal. Solvent extraction involves the use of organic solvents to extract the lipid components from the macadamia kernel to obtain the macadamia oil. To extract macadamia oil using supercritical $CO_2$, ground macadamia nuts are placed in an extraction vessel of a specialized extraction system and supercritical $CO_2$ is pumped through the material at carefully controlled temperature and pressure conditions. The $CO_2$ dissolves the oil components, which are then separated and collected by depressurizing the $CO_2$ stream, leaving behind the extracted macadamia oil as a liquid concentrate.

In some embodiments, macadamia oil comprises at least one selected from the group consisting of fatty acids, phytochemicals, and antioxidants. In one embodiment, the fatty acids are monounsaturated fatty acids. Suitable examples of monounsaturated fatty acids include, but are not limited to, oleic acid, palmitoleic acid, palmitic acid, vaccenic acid, elaidic acid, and cis-vaccenic acid. In a preferred embodiment, the macadamia oil comprises at least one selected from the group consisting of oleic acid, palmitoleic acid, and palmitic acid. Oleic acid may aid in the reduction of inflammation in the body by inhibiting pro-inflammatory cytokines, activating anti-inflammatory pathways, and reducing oxidative stress within the liver tissue. In another embodiment, the macadamia oil comprises oleic acid in an amount of 40 to 70 v/v % relative to a total volume of the macadamia oil. Palmitoleic acid may suppress inflammatory pathways by downregulating the expression of inflammatory markers (i.e., NF-κB) and promoting the activation of anti-inflammatory macrophages. In another embodiment, the macadamia oil comprises palmitoleic acid in an amount of 10 to 30 v/v % relative to a total volume of the macadamia oil. Palmitic acid may activate inflammatory pathways, particularly through the toll-like receptor 4 (TLR4) signaling cascade, leading to the production of pro-inflammatory cytokines like TNF-α and IL-6. In one embodiment, the macadamia oil comprises palmitic acid in an amount of 5 to 25 v/v % relative to a total volume of the macadamia oil. In another embodiment, the macadamia oil may further comprise phytochemicals (e.g., β-sitosterol, α-tocopherol, α-tocotrienols, ρ-hydroxybenzoic acid, and caffeic acid), antioxidants (e.g., tocopherols and phytosterols), and triacylglycerols (e.g., triolein, 1-palmitoyl-2,3-dioleoyl-glycerol, and 1-palmitoleoyl-2-oleoyl-3-stearoyl-glycerol)

In some embodiments, the macadamia oil nanoemulsion comprises 20 to 35 v/v % macadamia oil relative to a total volume of the macadamia oil nanoemulsion. In other embodiments, the macadamia oil nanoemulsion comprises 21 to 34 v/v % macadamia oil. In a preferred embodiment, the nanoemulsion comprises 25 v/v % of the macadamia oil.

In some embodiments, the macadamia oil nanoemulsion comprises a surfactant mixture comprising a hydrophilic emulsifier and a cosurfactant. In another embodiment, the macadamia oil nanoemulsion comprises a surfactant mixture in an amount of 15 to 40 v/v % relative to a total volume of the macadamia oil nanoemulsion, most preferably 1:1.

Suitable hydrophilic emulsifiers include, but are not limited to, polysorbate 20, polysorbate 40, polysorbate 60, polysorbate 80, polysorbate 85, polyoxyethylene sorbitan monolaurate, polyoxyethylene sorbitan monopalmitate, polyoxyethylene sorbitan monooleate, polyoxyethylene sorbitan monostearate, ceteth-20, ceteth-40, ceteth-60, ceteth-80, steareth-20, steareth-40, steareth-60, steareth-80, glyceryl stearate, PEG-12, PEG-30, PEG-40, PEG-60, PEG-100, PEG-150, PEG-200, ceteareth-20, ceteareth-40, ceteareth-60, ceteareth-80, sorbitan oleate, sorbitan laurate, sorbitan stearate, poloxamer 188, poloxamer 407, poloxamer 188R, polyvinyl alcohol, polyvinylpyrrolidone, ethoxylated castor oil, ethoxylated glycerin, ethoxylated lanolin, sodium lauryl sulfate, ammonium lauryl sulfate, cocamidopropyl betaine, sodium laureth sulfate, polyquaternium-7, polyquaternium-10, and polyquaternium-11. In a preferred embodiment, the hydrophilic emulsifier is a nonionic emulsifier. Nonionic emulsifiers are less hazardous to consume and have a lower critical micelle concentration than ionic emulsifiers, making them a preferred choice in the preparation of orally administered nanoemulsions. In some embodiments the hydrophilic emulsifier is a polysorbate. In one embodiment, the hydrophilic emulsifier is at least one selected from the group consisting of polysorbate 20, polysorbate 40, and polysorbate 80. In a preferred embodiment, the hydrophilic emulsifier is polysorbate 80. In some embodiments, the hydrophilic emulsifier is present in the surfactant mixture in an amount of 10 to 30 v/v % relative to a total volume of the macadamia oil nanoemulsion. In another embodiment, the hydrophilic emulsifier is present in the surfactant mixture in an amount of 10 to 30 v/v % relative to a total volume of the macadamia oil nanoemulsion.

Suitable cosurfactants include, but are not limited to, an ethylene glycol, a propylene glycol, a triethylene glycol, a diethylene glycol, butylene glycol, pentylene glycol, hexylene glycol, glycerin, dipropylene glycol, triethanolamine, urea, sorbitol, isopropyl alcohol, 1,3-butylene glycol, 2,3-butanediol, 1,2-propanediol, and/or combinations thereof. In some embodiments, the cosurfactant is at least one selected from the group consisting of the ethylene glycol, the propylene glycol, the triethylene glycol, and the diethylene glycol. In one embodiment, the cosurfactant is at least one selected from the group consisting of an ethylene glycol, a propylene glycol, a triethylene glycol, and a diethylene glycol. In a preferred embodiment, the cosurfactant is propylene glycol. In some embodiments, the cosurfactant is present in the surfactant mixture in an amount of 10 to 30 v/v % relative to a total volume of the macadamia oil nanoemulsion.

In some embodiments, the macadamia oil nanoemulsion comprises water. The water may be tap water, distilled water, bi-distilled water, deionized water, deionized distilled water, reverse osmosis water, hard water, fresh water, brine/salt water, hard water, and freshwater. In a preferred embodiment, the water is distilled water. In one embodiment, the macadamia oil nanoemulsion comprises 40 to 70 v/v % water relative to a total volume of the macadamia oil nanoemulsion. In some embodiments, the macadamia nanoemulsion comprises 41 to 64 v/v % water, most preferably 45 v/v % water relative to a total volume of the macadamia oil nanoemulsion.

In one embodiment, the macadamia oil nanoemulsion has an average droplet size of less than 200 nm, most preferably 134 nm or less.

In a preferred embodiment, the macadamia oil nanoemulsion has an average droplet size of 132.25±1.52 to 195.46±4.89 nm.

In one embodiment, the macadamia oil nanoemulsion has a PDI of less than 0.50. For an orally administered nanoemulsion, a desirable PDI may be considered to be below 0.5, indicating a uniform droplet size distribution and a homogenous nanoemulsion formulation, which may make the nanoemulsion more stable against creaming, flocculation, and coalescence. Flocculation may cause instability in a nanoemulsion because it leads to the clustering of individual droplets, effectively increasing their apparent size and making them more prone to further destabilization mechanisms like creaming, sedimentation, and eventually coalescence, ultimately causing phase separation and a potential loss of the desired properties of the nanoemulsion. Creaming may cause instability in a nanoemulsion because it leads to a visible separation of the dispersed phase (oil droplets) from the continuous phase (water), forming a concentrated layer at the top of the container, making the emulsion uneven and potentially compromising its intended properties and functionality. Coalescence may cause instability in a nanoemulsion by the tiny droplets within the emulsion merging together to form larger droplets, significantly reducing the overall surface area of the dispersed phase, potentially leading to phase separation and making the nanoemulsion ineffective for its intended purpose. Accordingly, a nanoemulsion having a low PDI is preferred because it may increase the stability of the nanoemulsion. In a preferred embodiment, the macadamia nanoemulsion has a PDI of 0.342±0.02.

In one embodiment, the macadamia oil nanoemulsion has an absolute zeta potential of −22.31±1.40 to −33.71±1.80. The absolute zeta potential of a nanoemulsion may indicate the stability of the nanoemulsion because the absolute zeta potential indicates the strength of repulsive force between particles. Accordingly, an increased absolute zeta potential, such as 20 to 60 mV, is preferred for a nanoemulsion because a higher absolute zeta potential indicates a decreased tendency of particles in a nanoemulsion to clump together, thus increasing stability of the nanoemulsion. In a preferred embodiment, the macadamia oil nanoemulsion has an absolute zeta potential of 33.71±1.80.

In one embodiment, the macadamia oil nanoemulsion has a viscosity of 2.57±0.61 to 8.67±0.45 cP. In orally administered nanoemulsions, the viscosity may impact the stability of the formulation by preventing creaming and sedimentation of the oil droplets, ensuring a consistent drug delivery and improving the oral bioavailability of drugs by allowing for prolonged contact with the mucosal lining of the gastrointestinal tract. In another embodiment, the macadamia oil nanoemulsion has a viscosity of 5.53±0.23 cP.

In one embodiment, the macadamia oil nanoemulsion has a creaming index of 0.52±0.03 to 3.16±0.98%. A lower creaming index may ensure a more stable nanoemulsion by achieving more consistent drug distribution and absorption upon oral administration because a low creaming index indicates the nanoemulsion droplets are well dispersed and more resistant to separation. A low creaming index for a nanoemulsion is considered to be a value between 0 to 20%. In some embodiments, the macadamia oil nanoemulsion has a creaming index of 1.22±0.25%.

In one embodiment, the macadamia oil nanoemulsion comprises spherical droplets. The spherical droplets in a macadamia oil nanoemulsion allows for even distribution of the oil droplets in the aqueous phase of the nanoemulsion and enhances stability by preventing droplet aggregation. Further, spherical droplets have a larger surface area, improving interactions between the nanoemulsion and the surrounding environment for better drug absorption and bioavailability.

In some embodiments, the macadamia oil nanoemulsion decreases the fatty degenerations and vacuolations seen in hepatic tissue of the subject compared to a macadamia oil. Thus, the macadamia oil nanoemulsion offers superior protection against liver congestion, dilation, and inflammation.

EXAMPLES

The following examples demonstrate a method of treating NAFLD. The examples are provided solely for illustration and are not to be construed as limitations of the present disclosure, as many variations thereof are possible without departing from the spirit and scope of the present disclosure.

Example 1: Effect of the Hydrophilic Emulsifier Type and Concentration on the Absolute Zeta Potential, Droplet Size, and PDI of the Macadamia Oil Nanoemulsion Macadamia oil was purchased from iHerb Company. Cholesterol was obtained from GFS chemicals and reagents from Powell, OH (USA), while bile salts were supplied by SAS chemicals Co. (Miumbai, India) and used for the preparation of the high-fat diet (HFD). Preparation of six O/W nanoemulsions was done using macadamia nut oil) at a concentration of 25 v/v %, and a hydrophilic emulsifier (Tween® 20, Tween® 40, Tween® 60, and Tween® 80) with different HLB values at different concentrations (5, 10 and 15 v/v %). The aqueous phase was prepared by dispersing the emulsifier on water using a magnetic stirrer at 300 rotations per minute (rpm) for 10 minutes (min). The oily phase was added to the aqueous phase slowly while homogenizing at 20,000 rpm for 15 min. Then, the prepared nanoemulsions were stored at 5° C. for 24 h. A factorial design was applied to the nanoemulsion formulations to find the optimized composition of the nanoemulsion formulations. A 2×3 factorial design was used for optimizing the macadamia oil nanoemulsion formulations. Two formulation factors (independent variables) were used, including the type of surfactant (X1), the concentration of the surfactant mixture (X2). X1 consisted of two surfactants: polysorbate 40 (Tween® 40) and polysorbate 80 (Tween® 80). X2 consisted of three surfactant mixture concentrations: 10 v/v %, 20 v/v %, and 30 v/v %. The effect of the independent variables in three dependent variables were analyzed, the dependent variables being the droplet size (Y1), the polydispersity index (Y2), and the zeta potential (ZP, Y3). Table 1 lists the selected dependent and independent variables.

TABLE 1

Independent and dependent variables of 2 × 3 factorial design for macadamia oil nanoemulsion

| Factors and responses | | Level Used | | |
|---|---|---|---|---|
| Factor | Name | Low (−1) | Medium(0) | High (±1) |
| A: X1 | Type of surfactant | Polysorbate 40 | . . . | Polysorbate 80 |
| B: X2 | Concentration of Surfactant mixture (%) | 10 | 20 | 30 |
| Response | Name | Goal | | |
| Y1 | Droplet size (nm) | Minimize | | |
| Y2 | Polydispersity index | Minimize | | |
| Y3 | Zeta potential (mV) | Maximize | | |

The droplet size, zeta potential, and PDJ of the nanoemulsion formulations were measured using dynamic light scattering with a Malvern Zetasizer. To determine the droplet size and their zeta potential, the samples were diluted with distilled water at a ratio of 1:100. The zeta potential values of the nanoemulsion formulations were obtained by assessing the electrophoretic mobility of oil droplets. The calculation of each parameter involved the use of triplicates.

Figure 1B:
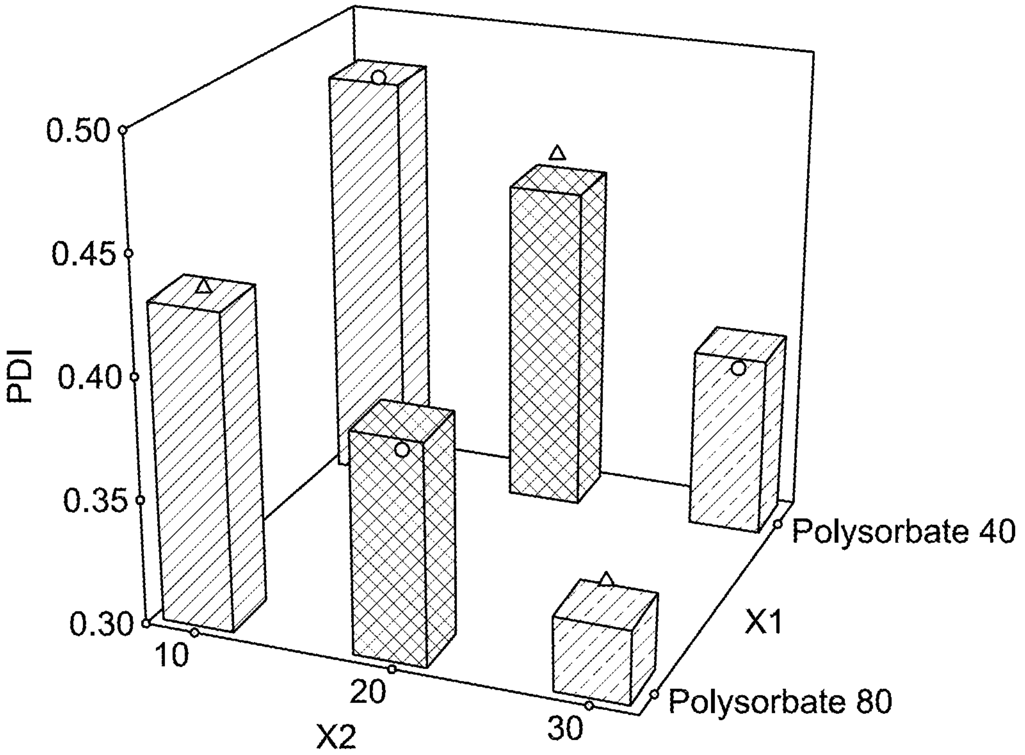
FIG. 1B is a graph depicting the effect of surfactant concentration and surfactant type on PDI, according to some embodiments.
Figure 1C:
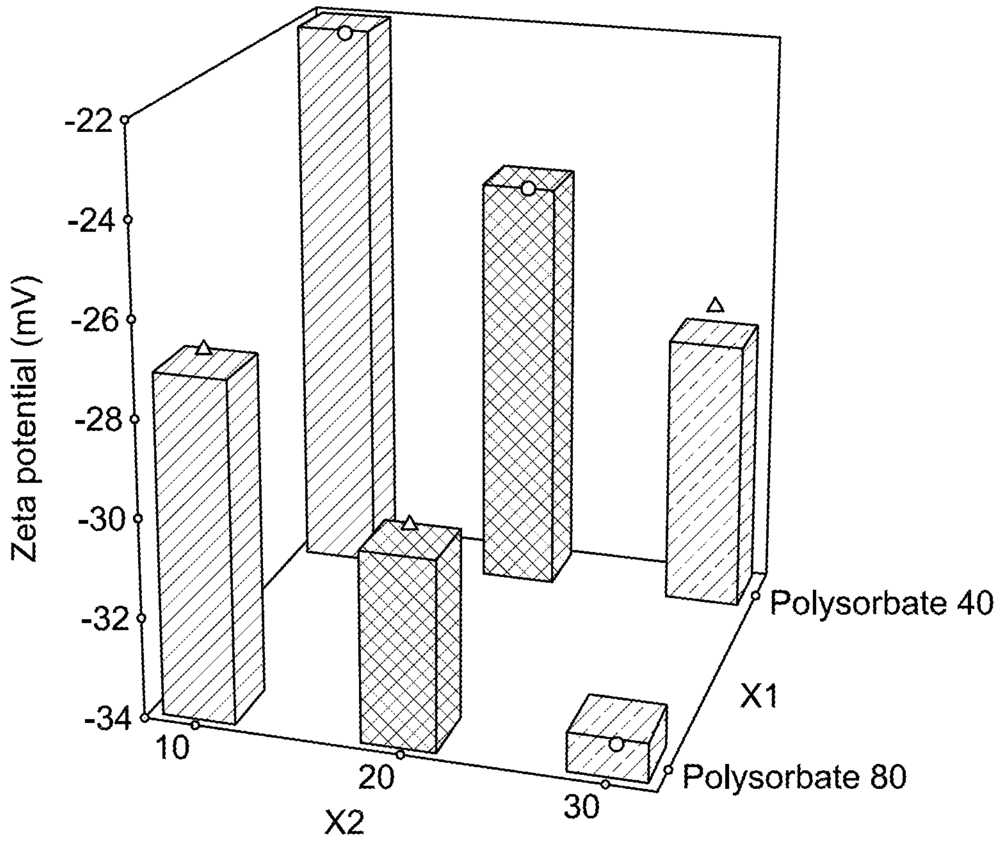
FIG. 1C is a graph depicting the effect of surfactant concentration and surfactant type on zeta potential, according to some embodiments.
Figure 2A:
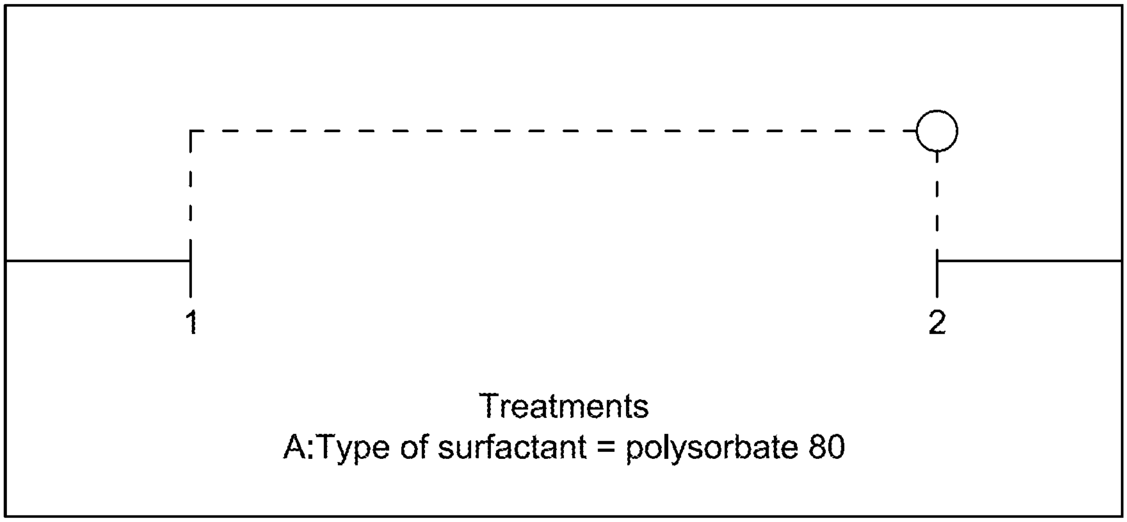
FIGS. 2A, 2B, 2C, 2D, and 2E show a dependent variable and an independent variable of an optimized macadamia oil nanoemulsion formulation, according to some embodiments.
Figure 2B:
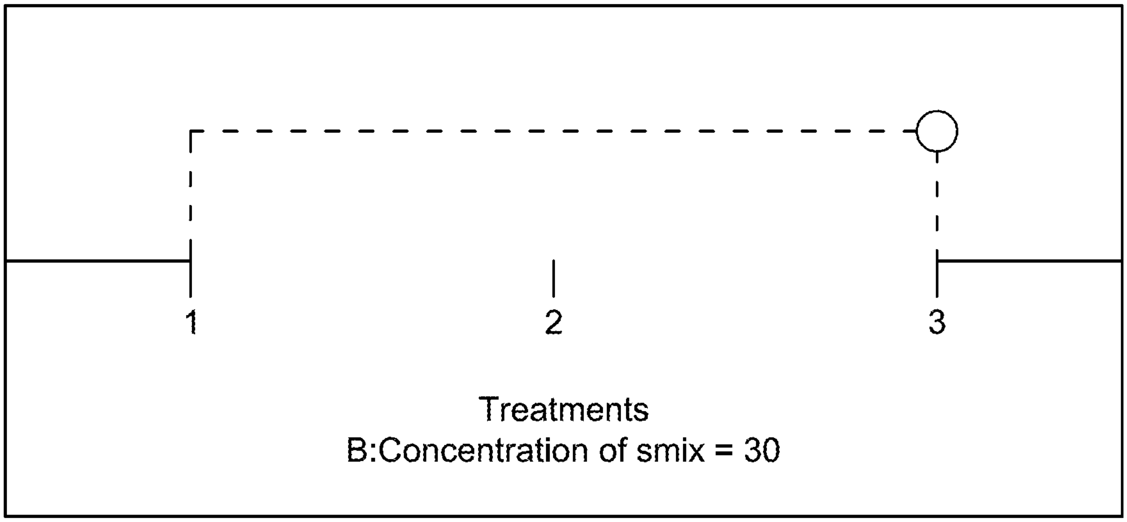
Figure 2C:
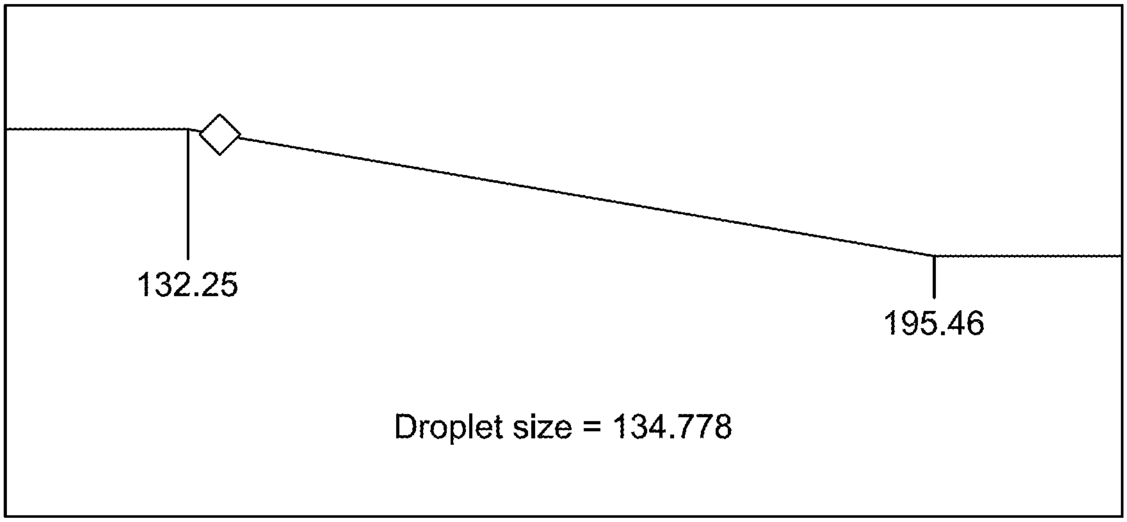
Figure 2D:
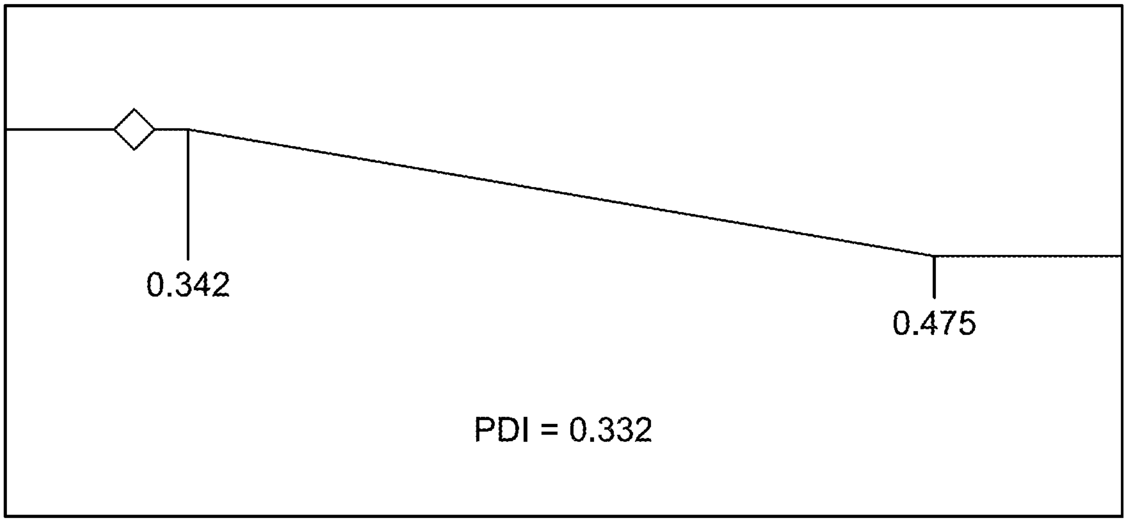
Figure 2E:
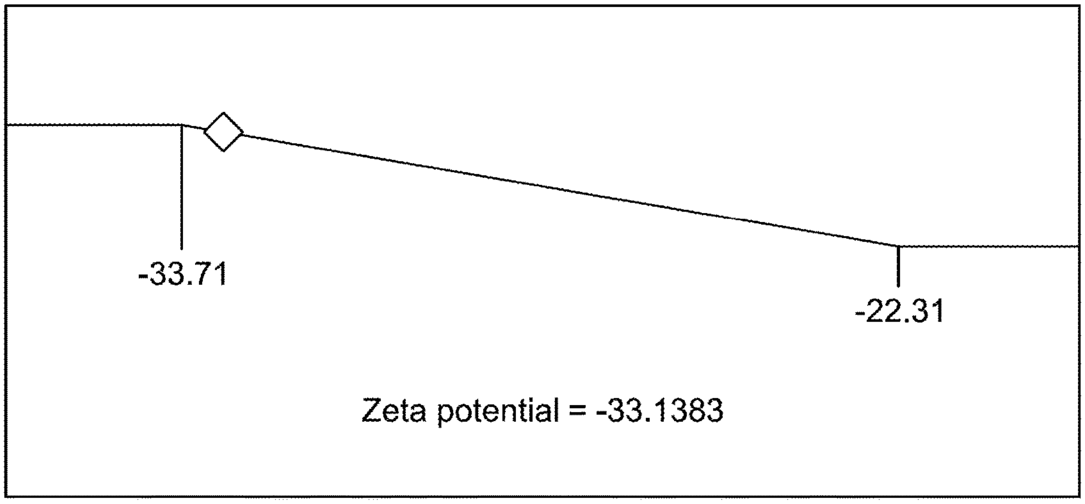

It was found that the droplet size was decreased in formulations prepared by polysorbate 80 rather than those prepared in the presence of polysorbate 40 (FIG. 1A). The observed results may be due to the difference in the HLB, where the HLB value of polysorbate 80 is 15, while for polysorbate 40, the HLB value is 15.6. In addition, as the concentration of the surfactant increased, a smaller droplet size was obtained (FIG. 1A). It was found that the PDI value decreased as the surfactant concentration increased, as shown in FIG. 1B. The PDI also decreased in formulations prepared in the presence of polysorbate 80 rather than polysorbate 40 (FIG. 1B). As can be seen from FIG. 1C, the negative zeta potential increased in formulations prepared in the presence of polysorbate 80 rather than polysorbate 40. Further, the zeta potential increased as the concentration of the surfactant increased. As provided in Table 2, it was found that the surfactant type (X1) had a significant effect on both droplet size (Y1) and zeta potential (Y3) ($p<0.05$) while surfactant concentration (X2) had a significant effect in all responses.

TABLE 2

ANOVA analysis for the effect of independent variables in the dependent variables of MC-NE formulations.

| Source | Sum of Squares | df | Mean Square | F-value | p-value | Comment |
|---|---|---|---|---|---|---|
| Response 1: Droplet size | | | | | | |
| Model | 2436.32 | 3 | 812.11 | 53.02 | 0.0186 | Significant |
| A - Type of surfactant | 966.47 | 1 | 966.47 | 63.09 | 0.0155 | |
| B - Concentration of Surfactant mixture | 1469.85 | 2 | 734.93 | 47.98 | 0.0204 | |
| Residual | 30.64 | 2 | 15.32 | | | |
| Cor Total | 2466.96 | 5 | | | | |
| Response 2: PDI | | | | | | |
| Model | 0.0133 | 3 | 0.0044 | 16.90 | 0.0564 | Not significant |
| A - Type of surfactant | 0.0030 | 1 | 0.0030 | 11.57 | 0.0766 | |
| B - Concentration of Surfactant mixture | 0.0103 | 2 | 0.0051 | 19.56 | 0.0486 | |
| Residual | 0.0005 | 2 | 0.0003 | | | |
| Cor Total | 0.0138 | 5 | | | | |
| Response 3: Zeta potential | | | | | | |
| Model | 74.58 | 3 | 24.86 | 50.70 | 0.0194 | Significant |
| A - Type of surfactant | 36.26 | 1 | 36.26 | 73.95 | 0.0133 | |
| B - Concentration of Surfactant mixture | 38.32 | 2 | 19.16 | 39.07 | 0.0250 | |
| Residual | 0.9806 | 2 | 0.4903 | | | |
| Cor Total | 75.56 | 5 | | | | |

Example 2: Preparation of Macadamia Oil Nanoemulsion (MC-NE) Formulations

Six formulations of MC-NE formulations were prepared by homogenization and ultrasonication methods. The aqueous phase was prepared through the dissolution of a precise quantity of surfactant (polysorbate 40 or polysorbate 80) and co-surfactant (propylene glycol) in double distilled water. 25 milliliters (mL) of macadamia oil were gradually introduced into the aqueous phase while homogenization was ongoing. The aforementioned process continued until the total amount of oil was reached. The homogenization was carried out using a high-shear homogenizer operating at a rotational speed of 20,000 rpm. The homogenization process was maintained for an additional duration of 15 minutes. The MC-NE formulations were subjected to sonication utilizing probe sonication for 5 minutes and thereafter stored at a temperature of 5° C. for 24 h before further analysis. The composition of MC-NE formulations is listed in Table 3. MC-NE formulations were prepared and evaluated for particle size, PDI, zeta potential, pH, viscosity, and creaming index.

TABLE 3

The composition of different formulations of MC-NE

| Formula No. | MC oil concentration (v/v %) | Surfactant type | Surfactant concentration (v/v %) | Propylene glycol (v/v %) | Water (v/v %) |
|---|---|---|---|---|---|
| MC-NE1 | 25 | Polysorbate 40 | 5 | 5 | 65 |
| MC-NE2 | 25 | Polysorbate 40 | 10 | 10 | 55 |
| MC-NE3 | 25 | Polysorbate 40 | 15 | 15 | 45 |
| MC-NE4 | 25 | Polysorbate 80 | 5 | 5 | 65 |
| MC-NE5 | 25 | Polysorbate 80 | 10 | 10 | 55 |

TABLE 3-continued

The composition of different formulations of MC-NE

| Formula No. | MC oil concentration (v/v %) | Surfactant type | Surfactant concentration (v/v %) | Propylene glycol (v/v %) | Water (v/v %) |
|---|---|---|---|---|---|
| MC-NE6 | 25 | Polysorbate 80 | 15 | 15 | 45 |

Example 3: Selection of Optimized MC-NE Based on Droplet Size, Polydispersity Index, Zeta Potential, Viscosity, Creaming Index, and pH The droplet size, zeta potential, and PDI of the nanoemulsion formulations were measured using dynamic light scattering with a Malvern Zetasizer. To determine the droplet size and their zeta potential, the samples were diluted with distilled water at a ratio of 1:100. The zeta potential values of the nanoemulsion formulations were obtained by assessing the electrophoretic mobility of oil droplets. The calculation of each parameter involved the use of triplicates.

As listed in Table 4, the droplet size of the prepared MC-NE formulations was in the range of 132.25±1.52 nm to 195.46±4.89 nm. It was further found that the PDI value for MC-NE formulations ranged from 0.342±0.02 to 0.475±0.01. All PDI values were less than 0.5, indicating the droplet size distribution homogeneity. All prepared MC-NE formulations exhibited a negative zeta potential in the range of −22.31±1.40 to −33.71±1.80 and an absolute value zeta potential of 22.31±1.40 to 33.71±1.80.

TABLE 4

Droplet size, PDI, and ZP of MC-NE formulations

| Formula No. | Y1: Droplet size (nm) | Y2: PDI | Y3: Zeta potential (mV) |
|---|---|---|---|
| MC-NE1 | 195.46 ± 4.89 | 0.475 ± 0.01 | −22.31 ± 1.40 |
| MC-NE2 | 181.91 ± 1.20 | 0.451 ± 0.02 | −25.44 ± 2.22 |
| MC-NE3 | 162.69 ± 4.47 | 0.367 ± 0.01 | −27.65 ± 1.36 |
| MC-NE4 | 175.99 ± 1.39 | 0.435 ± 0.01 | −26.67 ± 2.60 |
| MC-NE5 | 155.67 ± 3.08 | 0.381 ± 0.02 | −29.77 ± 1.83 |
| MC-NE6 | 132.25 ± 1.52 | 0.342 ± 0.02 | −33.71 ± 1.80 |

The viscosity of the MC-NE was measured by an Ostwald viscometer, the measurements were performed at a temperature of about 25±0.5° C. To measure, 10 mL of the sample was introduced into the larger bulb of the viscometer and subsequently drawn into the smaller bulb of the viscometer until it surpassed the upper demarcation on the instrument. Subsequently, the suction was terminated, and the sample was allowed to descend. The duration of passage of the sample, from the higher mark to the lower mark, in the smaller bulb was recorded. The measurement of flow time was repeated until a consistent viscosity value was determined. A viscosity test was conducted on all MC-NE formulations, with each formulation tested three times and mean±SD was calculated. Viscosity was calculated from flow time using the following equation, $$\eta_1 = \frac{\eta_2 t_1 \rho_1}{t_2 \rho_2}$$

where, '$\eta_1$' is viscosity of the MC-NE sample in cP, '$\eta_2$' is viscosity of the water in cP, '$t_1$' is flow time of the MC-NE sample in seconds, '$t_2$' is the water flow time in seconds, '$\rho_1$' is the density of MC-NE sample in g/cm$^3$, and '$\rho_2$' is the density of water in g/cm$^3$.

As provided in Table 5, the viscosity of MC-NEs was in the range of 2.57±0.61 to 8.67±0.45 cP. The viscosity was higher in formulations prepared in the presence of polysorbate 40 than those prepared with polysorbate 80. The increased viscosity may be attributed to the difference in HLB, where the HLB of Tween® 40 is 15.6, while for Tween® 80, the HLB is 15. The higher the HLB value of the surfactant, the higher the hydrophilicity, which led to the formation of hydrogen bonds between the hydrophilic portion of the surfactant and water molecules. The hydrogen bonds cause water molecules to be trapped within the cross-linking areas of the surfactant, resulting in a substantial viscosity increase. Further, it was found that the viscosity increases as the concentration of surfactant increases.

To measure the pH, the MC-NE preparations were homogenized with water at a ratio of 1:9, and further, the pH was measured using a pH meter from JENWAY, Staffordshire, UK. The measurements were performed in triplicate under standard environmental conditions. The pH value of MC-NE formulations was 6.16±0.07 to 6.98±0.12.

To measure the creaming index, each sample of the multiple MC-NE formulations was allocated about 50 mL and transferred into a glass bottle. The bottle was securely sealed with a cap, with a total of three replicates (n=3). Subsequently, the samples were subjected to accelerated conditions, specifically stored at temperatures of 4° C. and 45° C. for a total of six cycles and maintained for about 48 h in each temperature. The physical stability of the nanoemulsions was assessed by measuring the proportion of creaming and cracking. The phenomenon of nanoemulsion cracking manifests when there is a distinct separation between the oil and water components, preventing their recombination. The creaming index was measured by the following equation:

$$\text{Creaming index (\%)} = \frac{\text{cream layer height}}{\text{total emulsion height}} \times 100$$

As provided in Table 5, the CI % ranged from 0.52±0.03 to 3.16±0.98%. According to the obtained results, the CI % was inversely related to viscosity. The lower the CI %, the higher the physical stability of the nanoemulsion. The CI % decreased as the droplet size decreased, which may be attributed to the lower tendency of the oil droplets to move upward to form the cream. These larger droplets result in lower specific surface areas, being more susceptible to surface area fluctuations and increasing creaming and coalescence phenomena. Further, it was observed that CI % decreased as the zeta potential increased, which may be due to the repulsion between the oil droplets that possessed a negative charge. The CI % decreased by increasing the surfactant concentration, which may be attributed to the increase in stearic stability of the oil droplets and, hence, a decrease in the tendency to aggregate and coalescence. According to the visual observation, no formulation showed cracking of the emulsion.

TABLE 5 pH, viscosity, and CI % of the prepared MC-NE formulations

| Formula No. | pH | Viscosity (cP) | CI % |
|---|---|---|---|
| MC-NE1 | 6.79 ± 0.22 | 5.32 ± 0.32 | 1.62 ± 0.08 |
| MC-NE2 | 6.25 ± 0.14 | 6.88 ± 0.83 | 0.94 ± 0.02 |
| MC-NE3 | 6.16 ± 0.7 | 8.67 ± 0.45 | 0.52 ± 0.03 |
| MC-NE4 | 6.28 ± 0.17 | 2.57 ± 0.61 | 3.16 ± 0.98 |
| MC-NE5 | 6.98 ± 0.12 | 3.80 ± 0.46 | 2.66 ± 0.66 |
| MC-NE6 | 6.81 ± 0.11 | 5.53 ± 0.23 | 1.22 ± 0.25 |

Based on the numerical optimization using design expert software version 11 and the results of the experiment performed in Example 1 an optimized formulation of MC-NE was selected to have a small droplet size, a small PDI, and a high absolute zeta potential. As shown in FIG. 2A through FIGS. 2E, MC-NE6 was selected as the optimized formulation with polysorbate 80 (X1) and surfactant mixture concentration of 30 v/v % (X2). The predicted droplet size was 134.77 nm. Further, the predicted polydispersity index and zeta potential was 0.332 and −33.13 mV, respectively. It was found that the predicted values were close to the actual values of MC-NE6, with a desirability index of 0.970 which indicates the validity of the optimization process.

Figure 3:
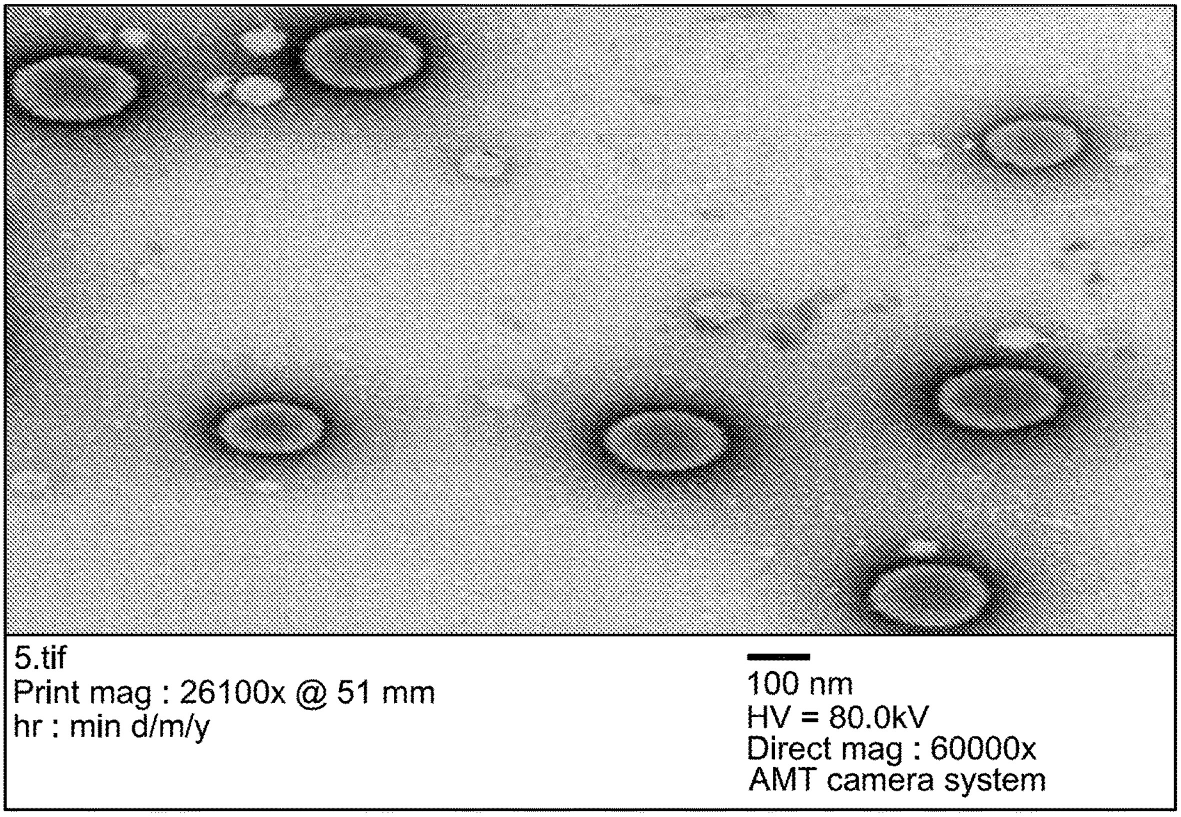
FIG. 3 is a transmission electron microscopy (TEM) image of the optimized macadamia oil nanoemulsion formulation, according to some embodiments.

Example 4: Transmission Electron Microscopy (TEM) Image of the Optimized MC-NE Formulation TEM was employed to examine the surface morphology of droplets of the MC-NE6 formulation. The sample was diluted with water at a ratio of 1:100, resulting in an oil phase concentration of 1 v/v %. One drop of diluted sample was added to copper coated collodion grid and allowed to be absorbed by the grid and dried further. Subsequently, the sample was stained by the addition of one drop of 2 w/v % uranyl acetate solution. Post-drying at room temperature, the sample was imaged with a JEOL transmission electron microscope (JTEM model 1010, JEOL®, Tokyo, Japan) at an accelerating voltage of 80 kilovolts (kV). The TEM image of the optimized formulation, MC-NE6, appeared with spherical oil droplets, as shown in FIG. 3. The contrast on the boundary may be related to the affinity of the uranyl acetate stain to the surfactant and cosurfactant on the interface.

Example 5: Methodology of Animal Experiment for Assessment of Biological Activity Adult male Wistar rats were used in the study. The body weight of the rats ranged from about 120 g to 150 g at the beginning of the experimentation. Rats were housed in plastic cages in groups of four, with free access to food and water for 12 weeks. Strict care, hygiene, and normal dark/light cycle were maintained for a healthy environment. The study protocol followed the ethical guidelines of the institutional research and ethics committee. Rats were fed with a high-fat diet (HFD) to induce the model of non-alcoholic fatty liver diseaes (NAFLD). Rats were randomly allocated to 4 groups, as follows:

(1) Normal rats: rats were maintained on the standard rat chow diet (2) Hepatic injury (HI) control rats: rats were maintained on a HFD. The diet composition was as follows: 87.7% basal rat chow mixed with 10% pork fat, 2% cholesterol, and 0.3% bile salts. The HFD was prepared every 5 days, divided into parts, kept at 4° C., and left at room temperature for 1 h before use.

(3) HI+macadamia oil group: rats were fed the HFD and received macadamia oil by oral gavage at 2 mL per rat, three times per week.

(4) HI+macadamia oil nanoemulsion group: Rats were fed with the HFD and received macadamia oil nanoemulsion (2 mL/rat) by oral gavage.

At the end of the experimental protocol, the body weights of the rats were measured. After overnight fasting, rats were anesthetized and sacrificed by applying the cervical dislocation procedure. Blood samples were withdrawn from the retro-orbital plexus and kept aside for 30 min, followed by centrifugation of the samples at 1500 rpm for 10 min. Serum samples were isolated and kept at −20° C. until use in different assays. Moreover, the livers were dissected and washed out of blood, dried on filter paper, and weighed. Data were collected, tabulated, and presented as the mean and standard deviation. Comparison between groups was achieved by application of the one-way ANOVA test and Bonferroni's test.

Example 6: Fasting Blood Sugar (FBS), Insulin, and Homeostatic Model Assessment for Insulin Resistance (HOMA-IR Index Measurements A spectrophotometric kit from Spinreact (Girona, Spain) was used for measuring FBS, while insulin was determined using an enzyme-linked immunosorbent assay (ELISA), rat insulin kit (Cat. No. RK03773, Woburn, MA, USA) based on competitive inhibition enzyme immunoassay. The minimum sensitivity of the assay was 50.2 picogram per milliliter (pg/mL), according to the determination protocol of the manufacturer. Utilizing an ELISA reader, the optical density of the final reaction product was measured to be about 450 nm. IR was determined using the HOMA-IR index using a formula:

$$HOMA\text{-}IR \text{ index} = \frac{\text{fasting glucose (mmol/L)} \times \text{fasting insulin } (\mu\text{U/mL})}{22.5}$$

Example 7: Assessment of Serum Liver Enzyme Activity

For evaluation of liver function, serum aspartate aminotransferase (AST) and alanine aminotransferase (ALT) activities were determined by enzymatic colorimetric assay kits using a spectrophotometer. Further, serum samples were frozen at −80° C. until used later. Serum levels of TNF-α and IL-1β were determined using ELISA kits, and fasting insulin was determined using an ultra-sensitive rat insulin ELISA kit. Furthermore, free fatty acids were determined using a free fatty acid (FFA) ELISA kit based on quantitative sandwich immunoassay and optical density measurement at 450 nm by ELISA reader. The kit sensitivity was 5.0 μmol/L within a detection range of 31.2 to 1000 micromole per liter (μmol/L).

Example 8: Liver Histopathology

The liver of the rats was dissected from and cut into tissue blocks, fixed in buffered formalin solution at a concentration of about 10%, over 24 h, and further dehydrated in ascending grades of alcohol 70%, 90%, 100%, 100%, 100% for 3 h each, followed by washing in xylene (3 changes for 2 h each). The livers were infiltrated by melted wax 65° C. (3 changes for 2 h each) and embedded in paraffin wax to form tissue blocks. Each tissue block was used to cut serial sections with 4 m thickness. For the examination, two sections were stained by hematoxylin and eosin.

Sections were visualized and rinsed gently in tap water. Lastly, the slides were dehydrated, cleared in xylene, and cover-slipped, further examined by light microscope (Olympus CX31). Furthermore, histopathological changes were assessed using a semiquantitative method, and each hepatic specimen was given a score according to the severity of the pathologic manifestations (Table 6).

TABLE 6

Criteria for classifying the degree of affection of hepatocytes.

| Degree of affection | Criteria |
|---|---|
| No affection | No morphological changes. |
| Mild affection | Swollen cells with pale cytoplasm (cloudy swelling). |
| Moderate affection | Vacuolated cytoplasm (Hydropic degeneration). |
| Moderate affection | Nuclear change with cytoplasmic affection (Necrosis) |

Figure 4A:
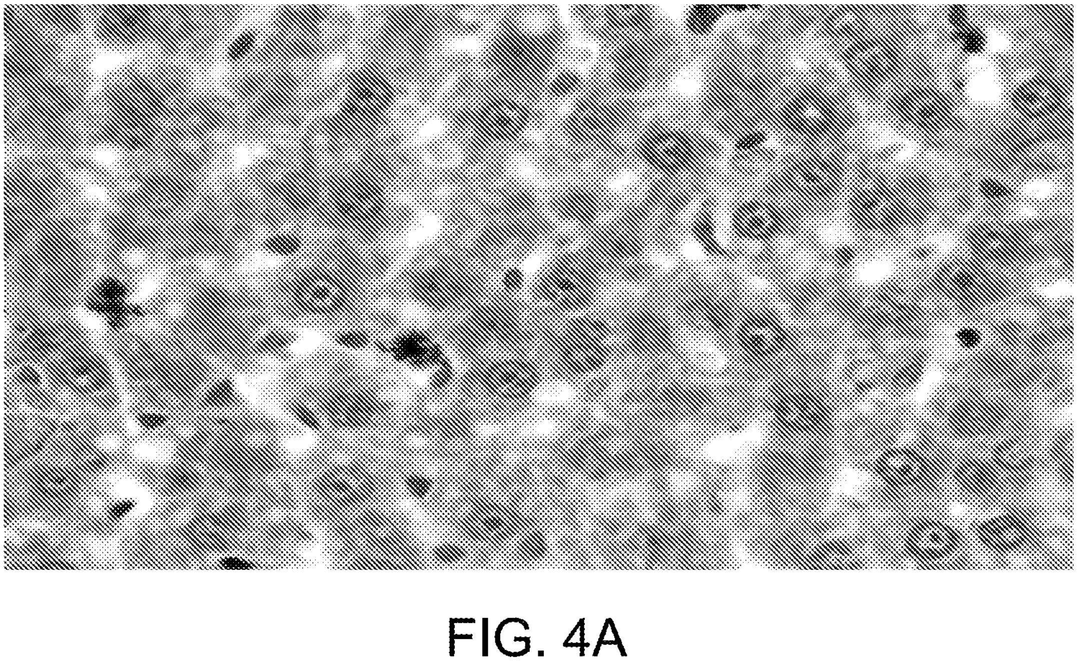
FIG. 4A shows a photomicrograph of hematoxylin and eosin stained liver tissue section from the normal group showing normal hepatocytes, according to certain embodiments.
Figure 4B:
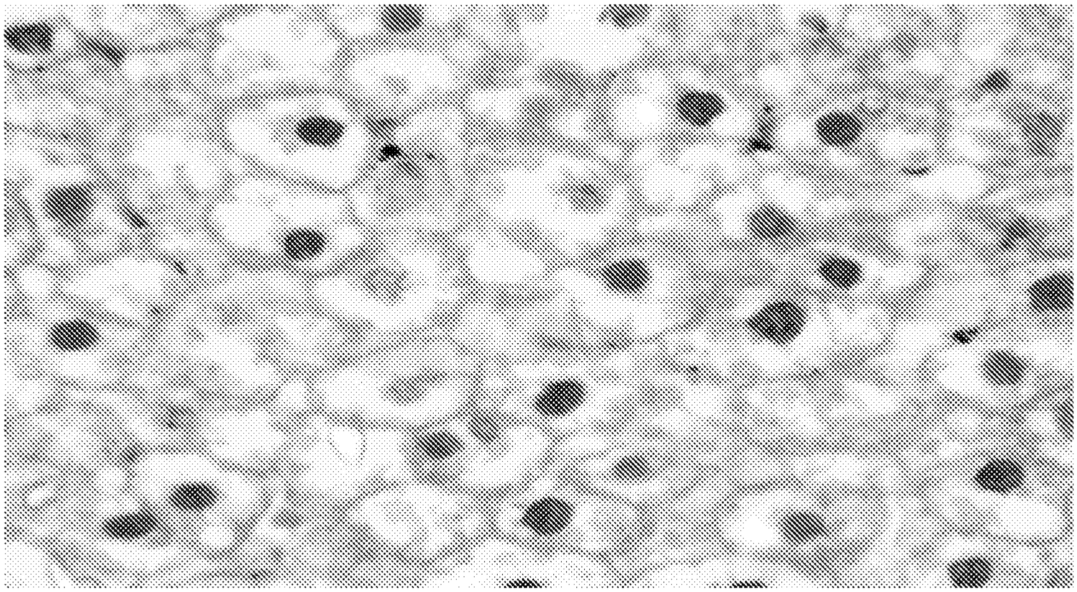
FIG. 4B shows a photomicrograph of hematoxylin and eosin stained liver tissue section from the hepatic injury group showing large fatty spaces, and cytoplasmic affection, according to certain embodiments.
Figure 4C:
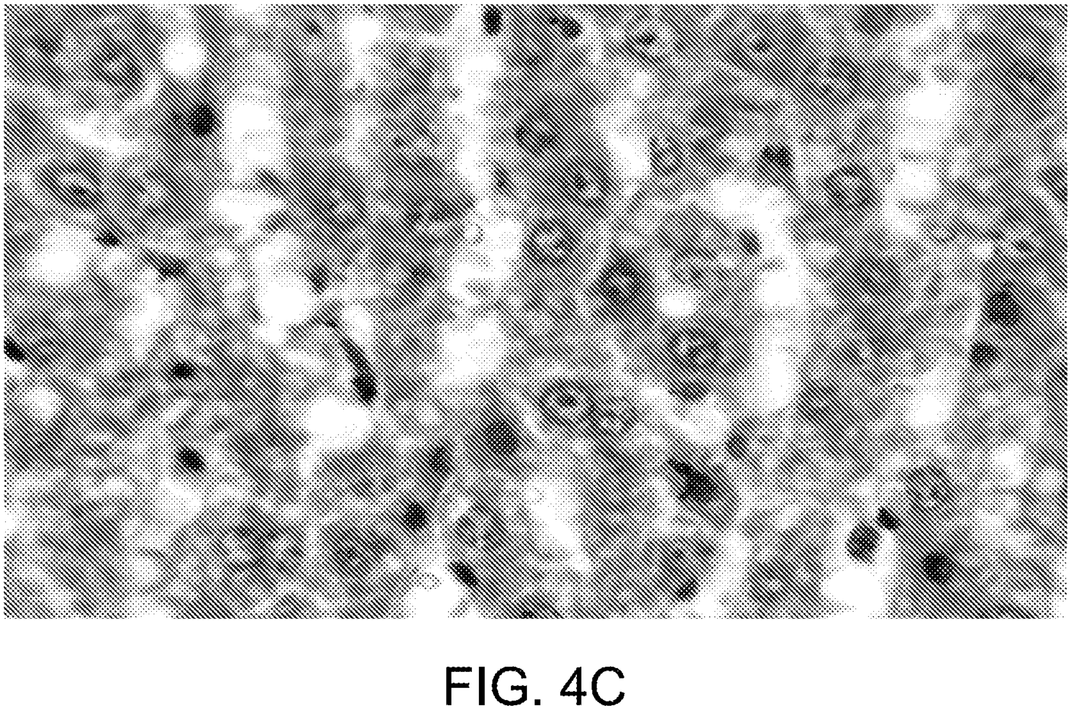
FIG. 4C shows a photomicrograph of hematoxylin and eosin stained liver tissue section from the hepatic injury group, which was treated with just macadamia oil showing medium fatty spaces, according to certain embodiments.
Figure 4D:
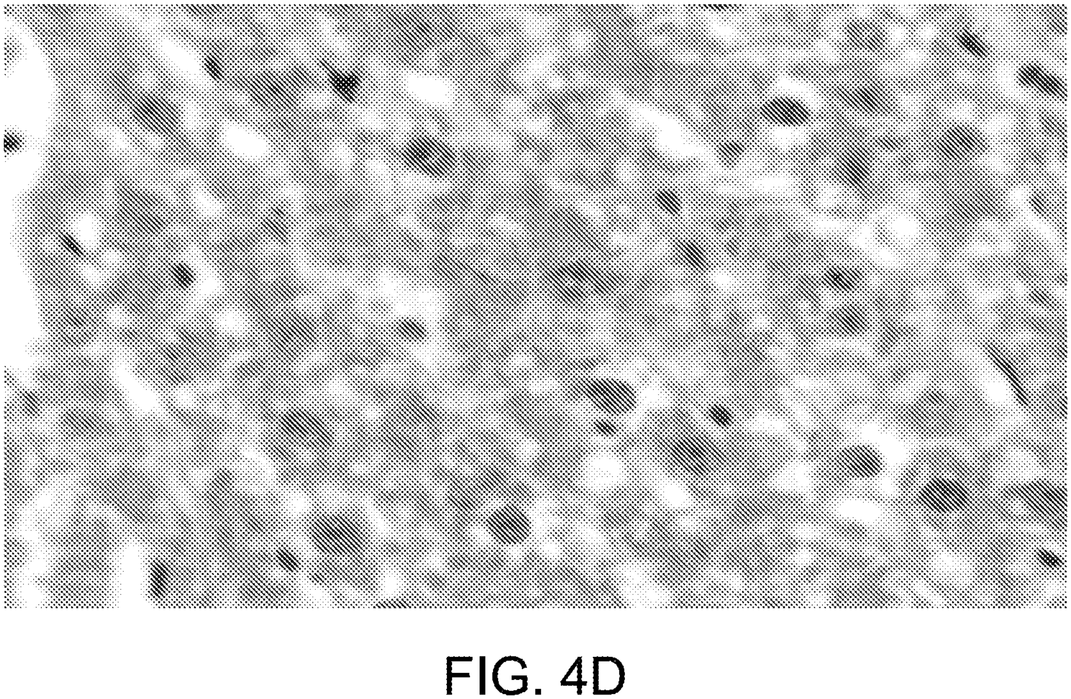
FIG. 4D shows a photomicrograph of hematoxylin and eosin stained liver tissue section from the hepatic injury group, which was treated with the macadamia oil nanoemulsion showing very minimal occurrence of fatty degenerations, according to certain embodiments.

Additionally, immunohistochemistry examinations were carried out on the liver segments from all groups. Examination of the normal group hepatic tissue stained with hematoxylin and eosin showed normal hepatocytes and visible nuclei as shown in FIG. 4A. Further, HI group examination of hematoxylin and eosin staining in the hepatic tissue depicted a marked increase in the number fatty spaces, vacuolation and inflammatory cells as shown in FIG. 4B. Furthermore, HI+macadamia oil group examination of hematoxylin and eosin stained hepatic tissue depicted a mild-moderate presence of fatty vacuoles as shown in FIG. 4C. Moreover, the HI+macadamia nanoemulsion (MC-NE6) group examination of hematoxylin and eosin stained hepatic tissue depicted a fewer number of fatty degenerated cells nearly similar to the normal group, as shown in FIG. 4D.

Numerous modifications and variations of the present disclosure are possible in light of the above teachings. It is therefore to be understood that within the scope of the appended claims, the invention may be practiced otherwise than as specifically described herein.

The invention claimed is:

1. A method of treating non-alcoholic fatty liver disease (NAFLD) in a patient in need thereof, comprising:

orally administering a therapeutically effective amount of a macadamia oil nanoemulsion to an NAFLD patient;

wherein the macadamia oil nanoemulsion comprises 25 v/v % of a macadamia oil, 15 v/v % polysorbate 80, 15 v/v % propylene glycol, and 45 v/v % water;

wherein the macadamia oil nanoemulsion has an average droplet size of 132.25±1.52 nm, a polydispersity index of 0.342±0.02, and an absolute zeta potential of −33.71±1.80 mV; and wherein administering the macadamia oil nanoemulsion to the patient at a dose of 0.8 mL/kg or less at least four times per week decreases liver tissue fatty degeneration and vacuolation relative to a control group of NAFLD patients treated by administering a matched dose of a macadamia oil composition that is not a nanoemulsion.

2. The method of claim 1, wherein the macadamia oil nanoemulsion has a viscosity of 2.57±0.61 to 8.67±0.45 cP.

3. The method of claim 1, wherein the macadamia oil nanoemulsion has a creaming index of 0.52±0.03 to 3.16±0.98%.

4. The method of claim 1, wherein the macadamia oil nanoemulsion comprises spherical droplets.

* * * * *